United States Patent [19]

Semrow

[11] Patent Number: 4,556,066

[45] Date of Patent: Dec. 3, 1985

[54] ULTRASOUND ACOUSTICAL COUPLING PAD

[75] Inventor: Carolyn M. Semrow, Island Lake, Ill.

[73] Assignee: The Kendall Company, Boston, Mass.

[21] Appl. No.: 548,633

[22] Filed: Nov. 4, 1983

[51] Int. Cl.⁴ .............................................. A61B 10/00
[52] U.S. Cl. ................................. 128/660; 128/661;
128/663; 128/639; 128/640
[58] Field of Search ................... 73/644; 128/663, 660,
128/639–641, 643, 661

[56] References Cited

U.S. PATENT DOCUMENTS

| 3,518,984 | 7/1970 | Mason | 128/640 |
| 3,834,373 | 9/1974 | Sato | 128/640 |
| 3,923,042 | 12/1975 | Hajou et al. | 128/641 |
| 4,002,221 | 1/1977 | Buchalter | 128/660 |
| 4,080,960 | 3/1978 | Goans et al. | 128/660 |
| 4,086,916 | 5/1978 | Freeman et al. | 128/663 |
| 4,313,444 | 2/1982 | Glenn | 128/663 |
| 4,355,643 | 10/1982 | Laughlin et al. | 128/663 |

Primary Examiner—Kyle L. Howell
Assistant Examiner—Ruth S. Smith
Attorney, Agent, or Firm—Powell L. Sprunger

[57] ABSTRACT

An ultrasound acoustical coupling pad comprising, a retaining member comprising a sheet having a front surface, a back surface, and a cut-out. The pad has a doppler transducer received in the cut-out, and a strip of acoustical gel covering at least a substantial portion of the front surface of the retaining member. The pad has a backing member comprising a sheet secured to the retaining member and having an edge portion extending outwardly from the retaining member and strip, with the edge portion having adhesive on a front surface thereof to secure the pad to the skin of a patient.

3 Claims, 2 Drawing Figures

ULTRASOUND ACOUSTICAL COUPLING PAD

BACKGROUND OF THE INVENTION

The present invention relates to ultrasound accustical coupling pads.

During certain procedures, it is necessary to continuously monitor doppler ultrasound signals on the body of a patient for extended periods of time. Accordingly, in the past the doppler transducer was taped to the body with gel on the transducer. However, the gel makes it very difficult for the tape to adhere to the skin. Also, if the transducer moves due to an unstable attachment by the tape the signal will change, and the transducer must be untaped, repositioned, and retaped with additional unused portions of tape.

SUMMARY OF THE INVENTION

A principal feature of the present invention is the provision of an improved ultrasound acoustical coupling pad of simplified construction.

The pad of the invention comprises a retaining member comprising a sheet having a front surface, a back surface, and a cut-out. The pad has a doppler transducer received in the cut-out, and a strip of acoustical gel covering at least a substantial portion of the front surface of the retaining member. The pad has a backing member comprising a sheet secured to the retaining member and having an edge portion extending outwardly from the retaining member and strip, with the edge portion having adhesive on a front surface thereof.

A feature of the present invention is that the adhesive on the edge portion may be utilized to secure the pad on a patient.

Thus, a feature of the present invention is that the pad may be secured in a simplified manner on a patient.

Another feature of the invention is that the strip of gel does not obstruct the adhesive on the edge portion during securement to a patient's body.

Yet another feature of the invention is that the backing member retains the doppler transducer securely in place adjacent the skin to eliminate the requirement of repositioning the transducer.

Further features will become more fully apparent in the following description of the embodiments of this invention and from the appended claims.

DESCRIPTION OF THE PREFERRED EMBODIMENTS

Figure 1:
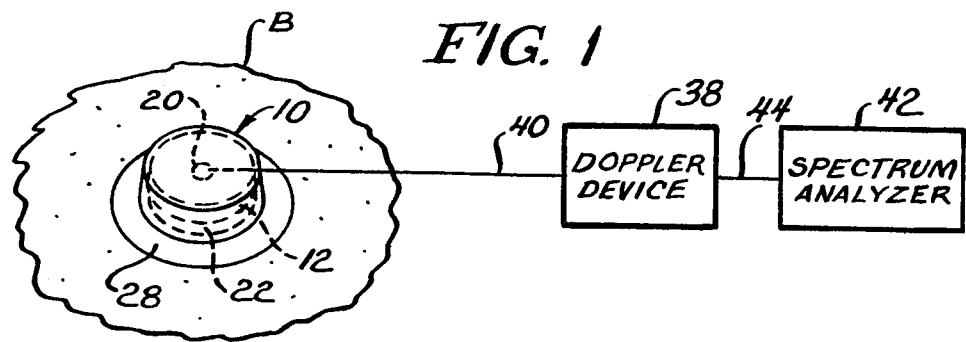
FIG. 1 is a perspective view illustrating an acoustical coupling pad of the present invention.
Figure 2:
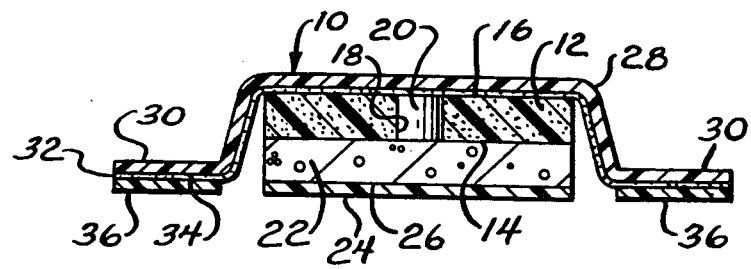
FIG. 2 is a sectional view of the pad of FIG. 1.

Referring now to FIGS. 1 and 2, there is shown an ultrasound acoustical coupling pad generally designated 10 for securement to a body B of a patient. The pad 10 has a circular retaining member 12 comprising a sheet of suitable material, such as foam, having a front surface 14, a back surface 16, and a cylindrical cut-out 18. As shown, a doppler transducer 20, such as a piezoelectric crystal, is positioned in the cut-out 18 in order to retain the transducer 20 in place.

The pad 10 has a circular strip 22 of acoustical gel of known type covering the front surface 14 of the retaining member 12. As shown, the pad 10 has a sheet 24 of flexible material releasably covering a front surface 26 of the gel strip 22.

The pad 10 has a backing member 28 comprising a sheet of flexible material, such as nonwoven material. The backing member 28 covers the back surface 16 of the retaining member 12, and has an edge portion 30 extending outwardly from the retaining member 12 and gel strip 22 peripherally around the retaining member 12 and strip 22. The backing member 28 has adhesive 32 on a front surface 34 of the backing member 28 in order to secure the backing member 28 to the back surface 16 of the retaining member 12 and retain the transducer 20 in place. Also, the edge portion 30 has adhesive 32 in order to secure the edge portion 30 to the patient's body B. The pad 10 has a release sheet 36 of known type releasably covering the adhesive 32 on the edge portion 30 of the backing member 28.

In use, the sheet 24 is removed from the gel strip 22 in order to expose the gel strip 22. Next, the release sheet 36 is removed from the edge portion 30 in order to expose the adhesive 32 on the edge portion 30. Finally, the pad 10 is secured to the body B of a patient at a desired location utilizing the adhesive 32 on the edge portion 30, with the gel strip 22 contacting the skin of the patient. The transducer 20 is electrically connected to a doppler device 38 by a conductive lead 40, and in turn the doppler device 38 is electrically connected to a spectrum analyzer 42 by a conductive lead 44. In this manner, the transducer 20 in conjunction with the doppler device 38 and spectrum analyzer 42 is utilized to detect the flow of blood in the patient.

In accordance with the present invention, the pad 10 may be attached to the skin of a patient in a simplified manner, and without obstruction of adhesive by the acoustical gel. Also, the pad 10 holds the transducer 20 firmly in place in order to eliminate the requirement that the transducer 20 be repositioned on the patient in the case that it moves.

The foregoing detailed description is given for clearness of understanding only, and no unnecessary limitations should be understood therefrom, as modifications will be obvious to those skilled in the art.

I claim:

1. An ultrasound acoustical coupling pad, comprising:
    a circular planar retaining member comprising a sheet of foam having a front surface free of adhesive on the front surface, a back surface, and a cut-out;
    a doppler transducer received in said cut-out and with the retaining member in direct contact with the transducer;
    a circular strip of acoustical gel covering the front surface of the retaining member;
    a sheet releasably covering a front surface of the strip;
    a backing member comprising a sheet of flexible material covering the entire back surface of the retaining member and having an exposed edge portion extending outwardly from the retaining member and strip peripherally around the retaining member and strip, said backing member having adhesive on a front surface thereof to secure the backing member to the back surface of the retaining member and secure the edge portion to the skin of a patient, said backing member overlying the transducer; and
    a release sheet releasably covering the adhesive on the edge portion of the backing member.

2. The pad of claim 1 including a doppler device electrically connected to said transducer.

3. The pad of claim 2 including a spectrum analyzer electrically connected to the doppler device.

* * * * *